United States Patent [19]

Zaiger et al.

[11] Patent Number: Plant 7,290

[45] Date of Patent: Aug. 7, 1990

[54] PEACH TREE "RICH LADY"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 342,359

[22] Filed: Apr. 24, 1989

[51] Int. Cl.[5] ..... A01H 5/00

[52] U.S. Cl. ..... Plt./43

[58] Field of Search ..... Plt./42, 43

*Primary Examiner*—Howard J. Locker

[57] ABSTRACT

A new and distinct variety of peach tree with the following unique combination of outstanding features that are desirable in a new variety:

1. Fruit with an attractive high red skin color.
2. Very firm fruit with excellent handling and shipping quality.
3. Large fruit size throughout the tree.
4. Fruit with very good flavor and eating quality.
5. Heavy and regular bearing of fruit.
6. Relatively uniform maturity of fruit throughout the tree.
7. Vigorous and upright growth.

1 Drawing Sheet

ORIGIN OF THE VARIETY

The present variety was originated by us in the experimental orchard located at Modesto, Calif., as a selected seedling from a large group of seedlings obtained from open pollinated Amparo Peach (U.S. Plant Pat. No. 6,472) seeds. The seedlings were planted and grown under careful and continual observation by us, during which time we recognized its distinct and desirable characteristics described above and selected the variety for reproduction and commercialization.

ASEXUAL REPRODUCTION OF THE VARIETY

Asexual reproduction of the new and distinct variety of peach tree was preformed by budding in the experimental orchard located at Modesto, Calif., shows that said characteristics run true to form and are established and transmitted through succeeding propagations.

SUMMARY OF THE VARIETY

The present variety relates to a new and distinct variety of peach tree which is of large size, vigorous, upright growth, and a regular and heavy producer of large, yellow flesh, clingstone fruit with good eating and shipping quality. The fruit is further characterized by having a high degree of attractive red skin color and having very firm flesh which allows the fruit to be harvest at near tree ripe maturity and still maintain good shipping and storage quality. The present variety of peach tree when compared to its seed parent, Amparo Peach (U.S. Plant Pat. No. 6,472) matures approximately 17 days earlier under similar cultural and climatic conditions.

BRIEF DESCRIPTION OF THE PHOTOGRAPHS

The accompanying photographs show reproductions in color of typical specimens of the foliage and fruit of the present variety, with the upper and lower surface of the leaves being illustrated and specimens of the fruit showing exterior skin color with one fruit being divided in the suture plane to show flesh color with the stone remaining in place.

DESCRIPTION OF THE VARIETY

The following is a detailed botanical description of the new peach tree, its flowers, foliage and fruit based on observations of specimens grown in the experimental orchard, located at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearing.*—Regular bearer.

Trunk:
- *Size.*—Large.
- *Texture.*—Shaggy.
- *Color.*—Brown to grayish brown.

Branches:
- *Size.*—Medium stocky.
- *Texture.*—Medium rough.
- *Color.*—Brown to reddish brown.

Leaves:
- *Size.*—Medium. Average length — $5\frac{1}{2}''$. Average width — $1\frac{1}{4}''$.
- *Texture.*—Smooth.
- *Margin.*—Crenate.
- *Petiole.*—Medium length. Medium thickness.
- *Glands.*—Reniform. Medium size. Number varies from 1 to 4. Average number 3. Located on the lower portion of the leaf blade and the upper part of the petiole.
- *Color.*—Upper surface — green (28-E-7) to (28-E-8). Lower surface — grayish green (28-E-5) to (28-E-6).

Flower buds:
- *Size.*—Large.
- *Form.*—Plump.
- *Pubescence.*—Pubescent.

Flowers:
- *Size.*—Large. Showy.
- *Blooming period.*—Feb. 24, 1987 to Mar. 3, 1987. Varies slightly with climatic conditions.
- *Pollen.*—Present.
- *Color.*—Pink, fades to very light pink at petal fall.

Fruit:

*Maturity when described.*—Firm ripe.
*Date of first picking.*—June 6, 1987.
*Date of last picking.*—June 13, 1987.
*Size.*—Large. Average diameter axially — $2\frac{5}{8}''$ to $2\frac{7}{8}''$. Average transversely in suture plane—$2\frac{3}{4}''$ to 3".
*Form.*—Nearly globose, slightly flattened at stem end.
*Ventral surface.*—Some fruit slightly enlarged near suture line.
*Suture.*—Shallow, distinct, extends from base to apex.
*Base.*—Retuse.
*Cavity.*—Rounded to slightly elongated in suture plane. Average depth — $\frac{1}{2}''$. Average breadth — 15/16".
*Apex.*—Rounded. Varies from slight pistol point to slight depression.

Skin:
*Thickness.*—Medium.
*Texture.*—Medium — tenacious to flesh.
*Tendency to crack.*—None.
*Down.*—Moderate to heavy.
*Color.*—Ground color — yellow to golden yellow — (4-A-8) to (5-A-6). Overspread with red to lake red — (9-B-8) to (9-C-8).

Flesh:
*Texture.*—Very firm.
*Ripens.*—Even.
*Juice.*—Moderate.
*Flavor.*—Very good — subacid to mild.
*Eating quality.*—Very good.
*Color.*—Yellow to golden yellow — (5-A-6) to (5-A-8). Stone Cavity — red to crayfish red — (9-A-7) to (9-B-8).
*Amygdalin.*—Undetected.
*Fibers.*—Few — tender.
*Aroma.*—Moderate to heavy.

Stone:
*Size.*—Large. Average length — $1\frac{1}{2}''$. Average width — $1\frac{1}{8}''$. Average breadth — $\frac{3}{4}''$.
*Type.*—Clingstone.
*Form.*—Ovid.
*Size.*—Mostly equal.
*Apex.*—Acuminate.
*Base.*—Usually straight — some round.
*Surface.*—Irregularly furrowed toward apex with the longest furrows near the outer edges and pitted toward the base.
*Ridges.*—Rounded.
*Tendency to split.*—Very slight.
*Color.*—Reddish brown — (8-D-7) to brownish red — (9-C-7).

Use: Dessert.
*Market.*—Local and long distance.
Keeping quality: Very good.
Shipping quality: Excellent.

The present new variety of peach tree, its fruit and foliage herein described may vary in slight detail due to climatic, soil conditions and cultural practices under which the variety may be grown; the present description is that of the variety grown in the experimental orchard at Modesto, Calif.

We claim:

1. A new and distinct variety of peach tree, as illustrated and described, characterized by its large size, vigorous upright growth and a regular and productive bearer of large, yellow flesh, clingstone fruit with very good flavor and eating quality, the fruit is further characterized by having very firm flesh and maintaining good handling and shipping quality while being harvested near tree ripe, having an attractive red skin color and matures approximately 17 days earlier than its seed parent Amparo Peach (U.S. Plant Pat. No. 6,472).

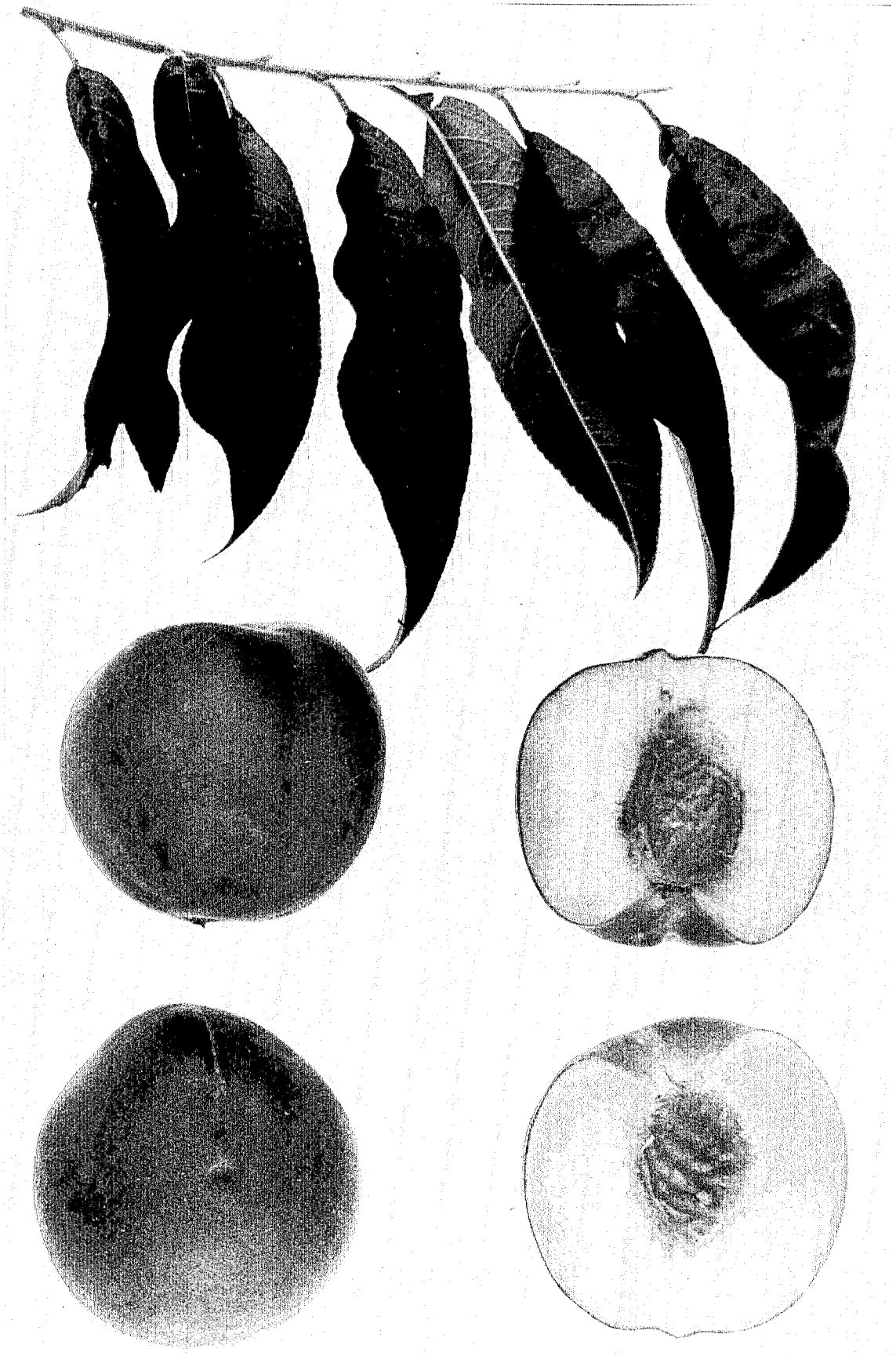

* * * * *